(12) United States Patent
Kalmann et al.

(10) Patent No.: US 7,811,316 B2
(45) Date of Patent: Oct. 12, 2010

(54) DEVICE FOR REGULATING BLOOD FLOW

(75) Inventors: Menno Kalmann, Elspeet (NL); Peter W. J. Hinchliffe, Campbell, NY (US); Adam I. Lehman, Northford, CT (US)

(73) Assignee: Deep Vein Medical, Inc., Boston, MA (US)

( * ) Notice: Subject to any disclaimer, the term of this patent is extended or adjusted under 35 U.S.C. 154(b) by 304 days.

(21) Appl. No.: 11/801,691

(22) Filed: May 10, 2007

(65) Prior Publication Data

US 2007/0288086 A1 Dec. 13, 2007

Related U.S. Application Data

(60) Provisional application No. 60/808,406, filed on May 25, 2006, provisional application No. 60/809,483, filed on May 31, 2006.

(51) Int. Cl.
*A61F 2/06* (2006.01)

(52) U.S. Cl. ..................... 623/1.24; 623/1.42

(58) Field of Classification Search ............... 623/1.12, 623/1.14, 1.15, 1.17, 1.24, 1.36, 23.66, 23.68; 606/198, 200

See application file for complete search history.

(56) References Cited

U.S. PATENT DOCUMENTS

| | | |
|---|---|---|
| 3,589,392 A | 6/1971 | Meyer |
| 3,671,979 A | 6/1972 | Moulopoulos |
| 4,218,782 A | 8/1980 | Rygg |
| 4,759,758 A | 7/1988 | Gabbay |
| 4,787,901 A | 11/1988 | Baykut |
| 4,994,077 A | 2/1991 | Dobben |
| 5,104,404 A * | 4/1992 | Wolff ..................... 623/1.16 |
| 5,358,518 A | 10/1994 | Camilli |
| 5,500,014 A | 3/1996 | Quijano et al. |
| 5,607,465 A | 3/1997 | Camilli |
| 5,855,601 A | 1/1999 | Bessler et al. |
| 5,957,949 A | 9/1999 | Leonhardt et al. |

(Continued)

FOREIGN PATENT DOCUMENTS

EP 0520126 12/1992

(Continued)

OTHER PUBLICATIONS

International Search Report for PCT/US2009/000001, dated Apr. 8, 2009.

(Continued)

*Primary Examiner*—Corrine M McDermott
*Assistant Examiner*—Matthew Schall
(74) *Attorney, Agent, or Firm*—Edwards Angell Palmer & Dodge LLP

(57) ABSTRACT

An elongated support dimensioned and configured for implantation in a blood vessel. The support has two axially spaced apart portions, which may be in the form of an expandable crown or a similar structure. At least one linking member connects the two portions to one another. A valve membrane is supported between the axially spaced apart portions. The valve membrane is adapted and configured for movement between a first position in which blood flow through the support is permitted and a second position in which blood flow through the support is inhibited.

21 Claims, 16 Drawing Sheets

U.S. PATENT DOCUMENTS

| | | | |
|---|---|---|---|
| 6,027,525 A | 2/2000 | Suh et al. | |
| 6,110,201 A | 8/2000 | Quijano et al. | |
| 6,132,457 A | 10/2000 | Chobotov | |
| 6,200,336 B1 | 3/2001 | Pavcnik et al. | |
| 6,270,526 B1 | 8/2001 | Cox | |
| 6,287,334 B1 * | 9/2001 | Moll et al. | 623/1.24 |
| 6,299,637 B1 | 10/2001 | Shaolian et al. | |
| 6,315,793 B1 | 11/2001 | Bokros et al. | |
| 6,425,855 B2 | 7/2002 | Tomonto | |
| 6,440,164 B1 * | 8/2002 | DiMatteo et al. | 623/1.24 |
| 6,458,153 B1 | 10/2002 | Bailey et al. | |
| 6,482,228 B1 | 11/2002 | Norred | |
| 6,503,272 B2 | 1/2003 | Duerig et al. | |
| 6,517,576 B2 | 2/2003 | Gabbay | |
| 6,562,068 B2 | 5/2003 | Drasler et al. | |
| 6,569,198 B1 | 5/2003 | Wilson et al. | |
| 6,572,652 B2 | 6/2003 | Shaknovich | |
| 6,585,761 B2 | 7/2003 | Taheri | |
| 6,602,286 B1 * | 8/2003 | Strecker | 623/1.24 |
| 6,605,112 B1 | 8/2003 | Moll et al. | |
| 6,652,578 B2 | 11/2003 | Bailey et al. | |
| 6,676,699 B2 | 1/2004 | Shiu | |
| 6,752,828 B2 | 6/2004 | Thornton | |
| 6,767,362 B2 | 7/2004 | Schreck | |
| 6,869,444 B2 | 3/2005 | Gabbay | |
| 6,951,571 B1 | 10/2005 | Srivastava | |
| 6,974,474 B2 * | 12/2005 | Pavcnik et al. | 623/1.24 |
| 6,979,350 B2 | 12/2005 | Moll et al. | |
| 7,081,131 B2 * | 7/2006 | Thornton | 623/1.24 |
| 7,087,089 B2 | 8/2006 | Patel et al. | |
| 7,153,324 B2 | 12/2006 | Case et al. | |
| 7,201,772 B2 * | 4/2007 | Schwammenthal et al. | 623/2.18 |
| 7,270,675 B2 | 9/2007 | Chun et al. | |
| 7,361,189 B2 * | 4/2008 | Case et al. | 623/1.24 |
| 2001/0010017 A1 | 7/2001 | Letac et al. | |
| 2001/0039450 A1 | 11/2001 | Pavcnik et al. | |
| 2002/0099439 A1 | 7/2002 | Schwartz et al. | |
| 2003/0055492 A1 | 3/2003 | Shaolian et al. | |
| 2003/0130726 A1 | 7/2003 | Thorpe et al. | |
| 2003/0208261 A1 | 11/2003 | Thorpe et al. | |
| 2003/0209835 A1 | 11/2003 | Chun et al. | |
| 2004/0019374 A1 | 1/2004 | Hojeibane et al. | |
| 2004/0093070 A1 * | 5/2004 | Hojeibane et al. | 623/1.15 |
| 2004/0117004 A1 | 6/2004 | Osborne et al. | |
| 2004/0186558 A1 | 9/2004 | Pavcnik et al. | |
| 2004/0193253 A1 | 9/2004 | Thorpe et al. | |
| 2004/0210301 A1 | 10/2004 | Obermiller | |
| 2004/0215339 A1 | 10/2004 | Drasler et al. | |
| 2004/0225352 A1 | 11/2004 | Osborne et al. | |
| 2004/0260389 A1 | 12/2004 | Case et al. | |
| 2005/0059923 A1 | 3/2005 | Gamboa | |
| 2005/0096735 A1 | 5/2005 | Hojeibane et al. | |
| 2005/0137701 A1 | 6/2005 | Salahieh et al. | |
| 2005/0187614 A1 | 8/2005 | Agnew | |
| 2005/0203617 A1 | 9/2005 | Forster et al. | |
| 2005/0273159 A1 | 12/2005 | Opie | |
| 2006/0058889 A1 | 3/2006 | Case et al. | |
| 2006/0089708 A1 * | 4/2006 | Osse et al. | 623/1.24 |
| 2006/0106454 A1 | 5/2006 | Osborne et al. | |
| 2006/0136044 A1 | 6/2006 | Osborne et al. | |
| 2006/0190074 A1 | 8/2006 | Hill et al. | |
| 2006/0210597 A1 | 9/2006 | Hiles | |
| 2006/0259136 A1 * | 11/2006 | Nguyen et al. | 623/2.18 |
| 2006/0265053 A1 | 11/2006 | Hunt | |
| 2006/0282157 A1 | 12/2006 | Hill et al. | |
| 2007/0260327 A1 | 11/2007 | Case et al. | |
| 2007/0288086 A1 | 12/2007 | Kalmann et al. | |
| 2009/0018636 A1 | 1/2009 | Gailloud et al. | |

FOREIGN PATENT DOCUMENTS

| | | |
|---|---|---|
| WO | 0154625 | 8/2001 |
| WO | WO 02089869 A2 * | 11/2002 |

OTHER PUBLICATIONS

Written Opinion of the International Searching Authority for PCT/US2009/000001, dated Apr. 8, 2009.

International Preliminary Report on Patentability for PCT/US2007/020449 dated Nov. 10, 2009.

* cited by examiner

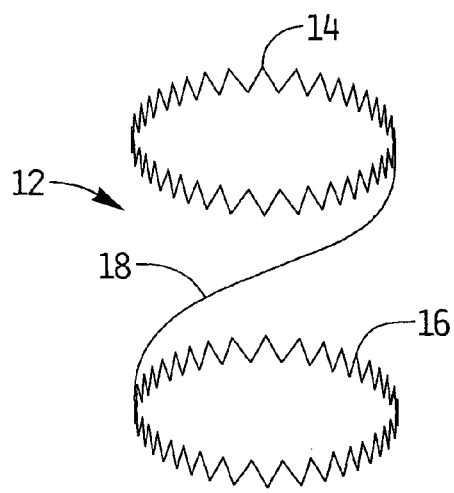
FIG_1
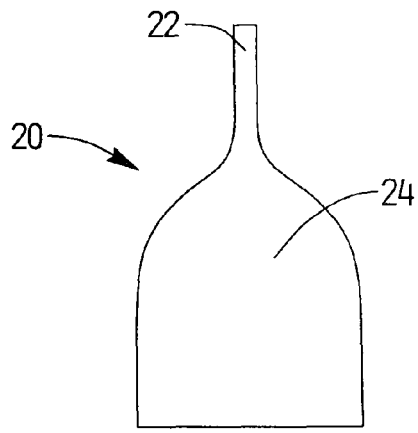
FIG_2
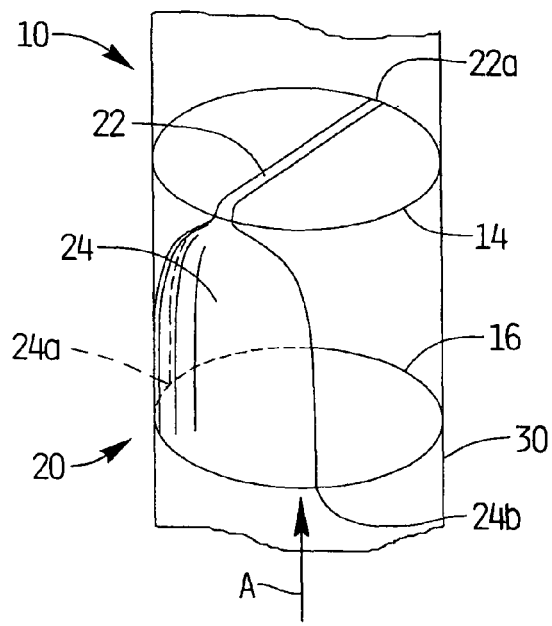
FIG_3
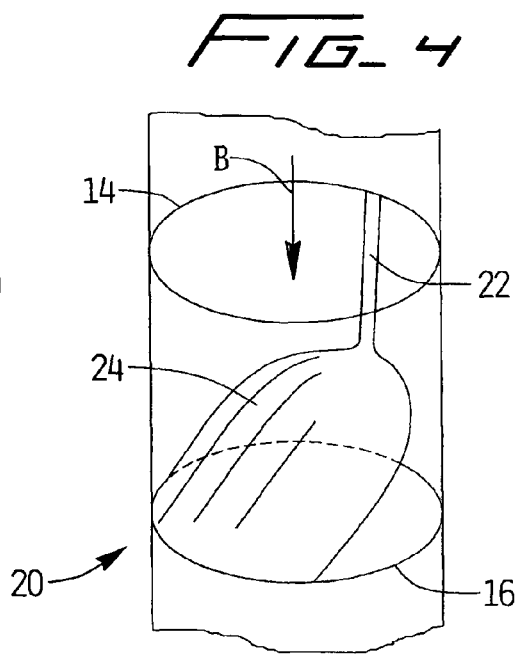
FIG_4

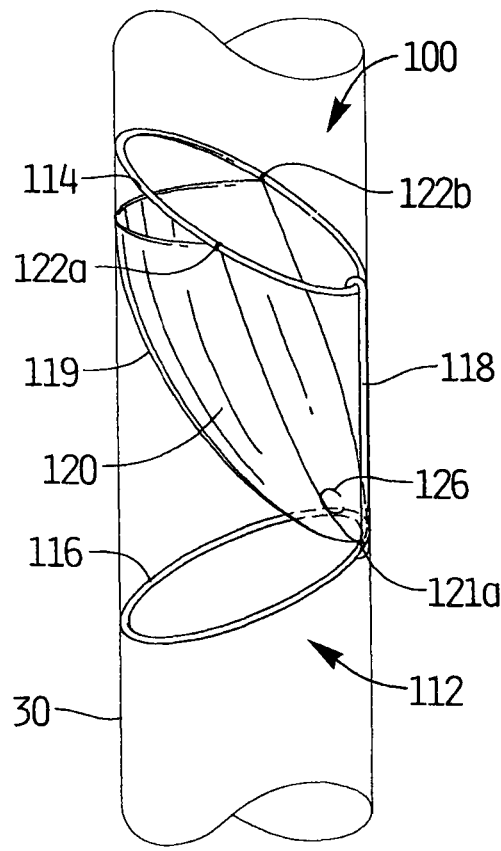
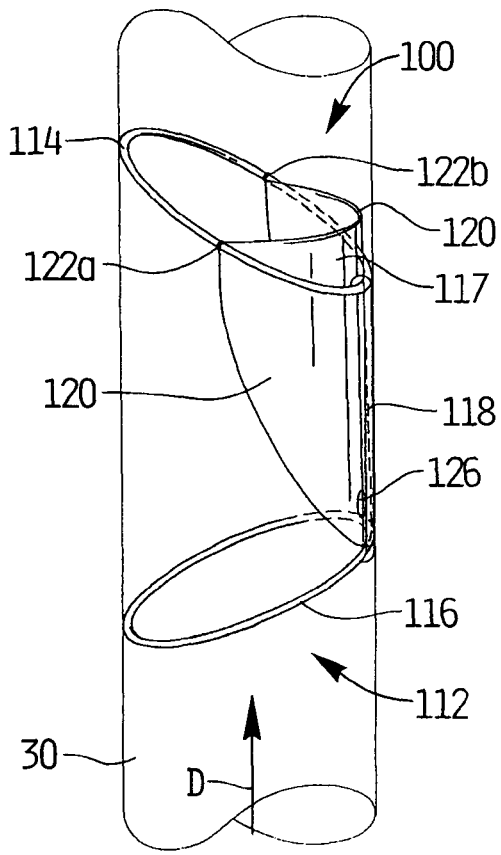

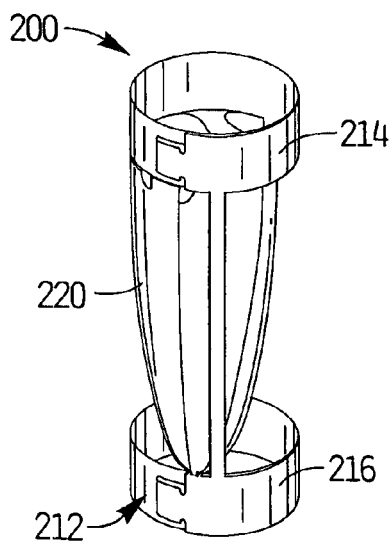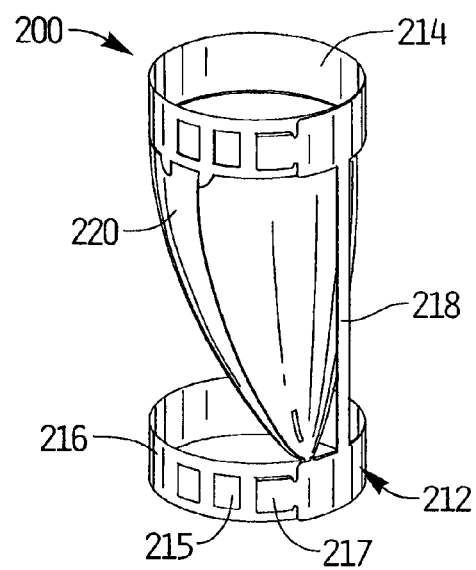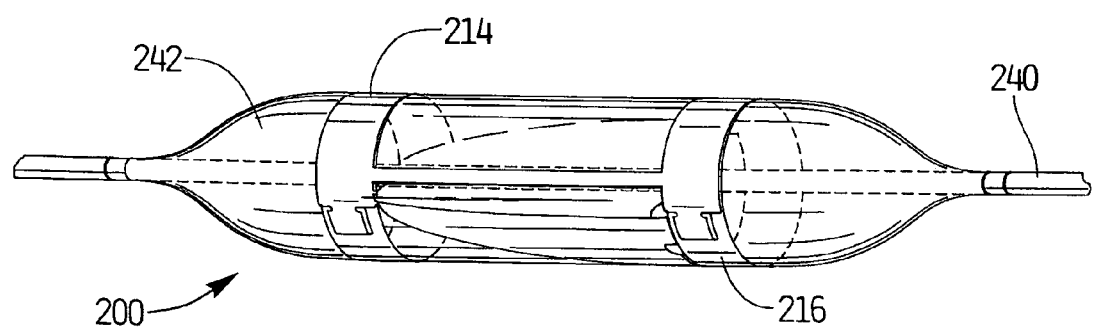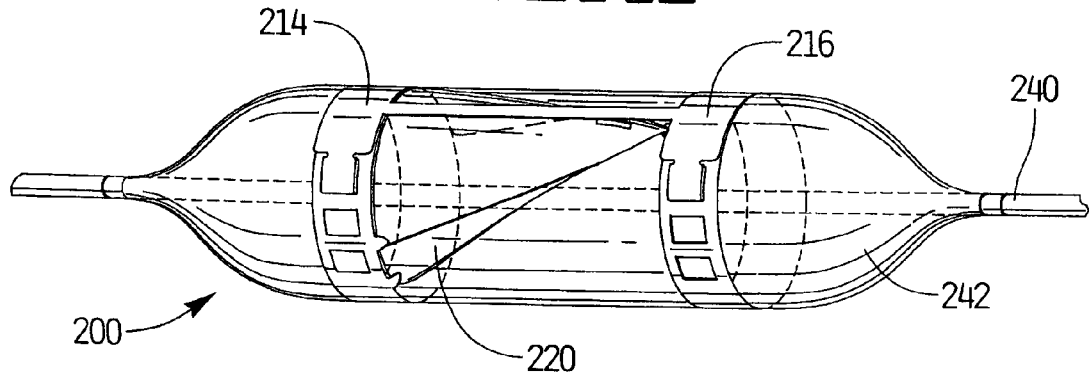

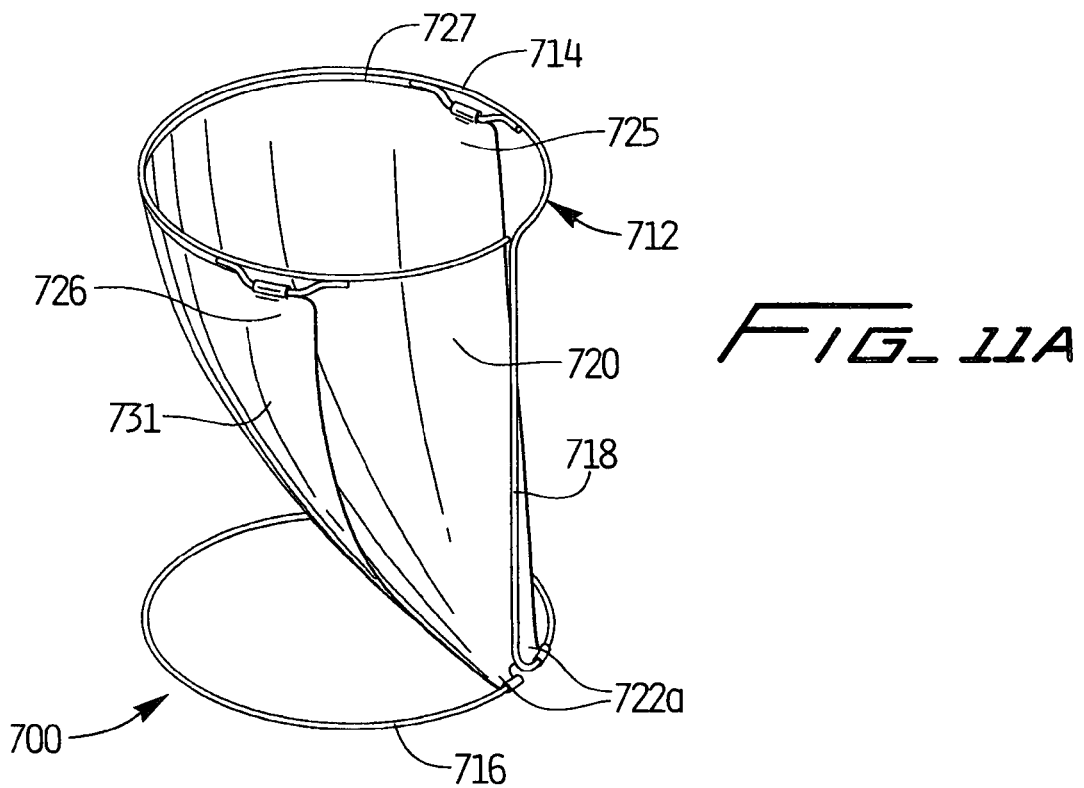
FIG_11A
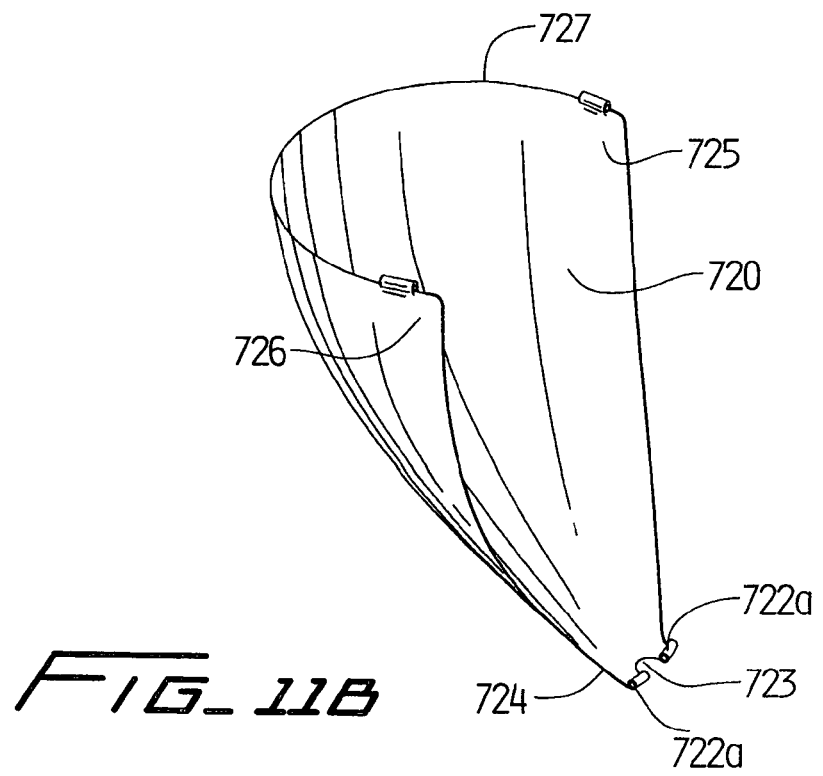
FIG_11B

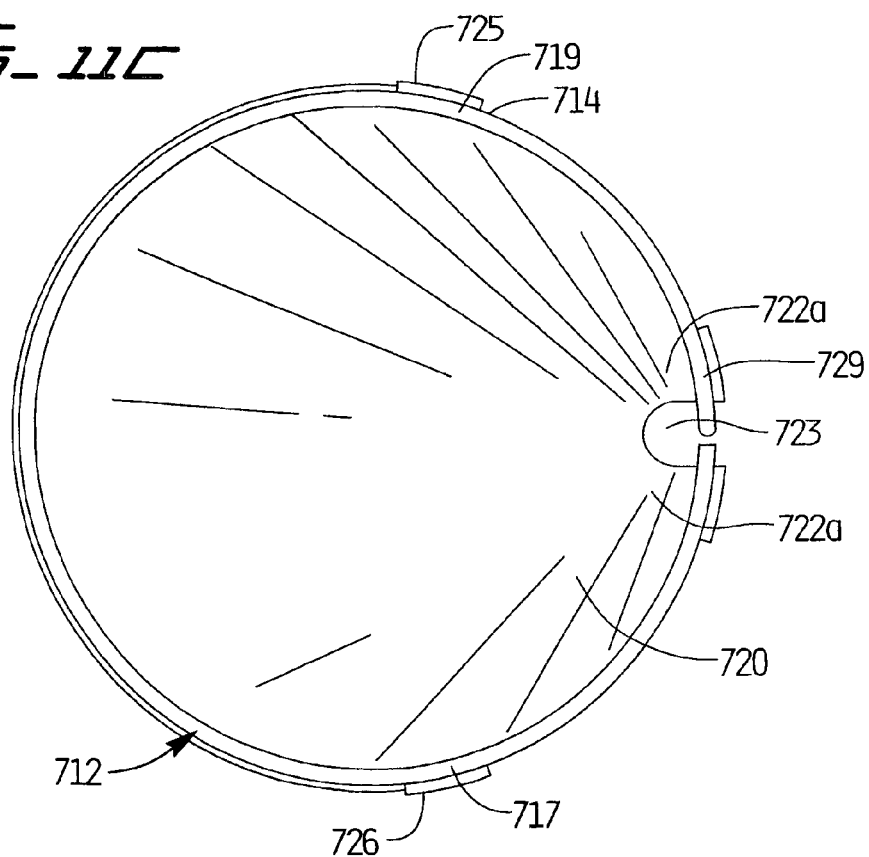
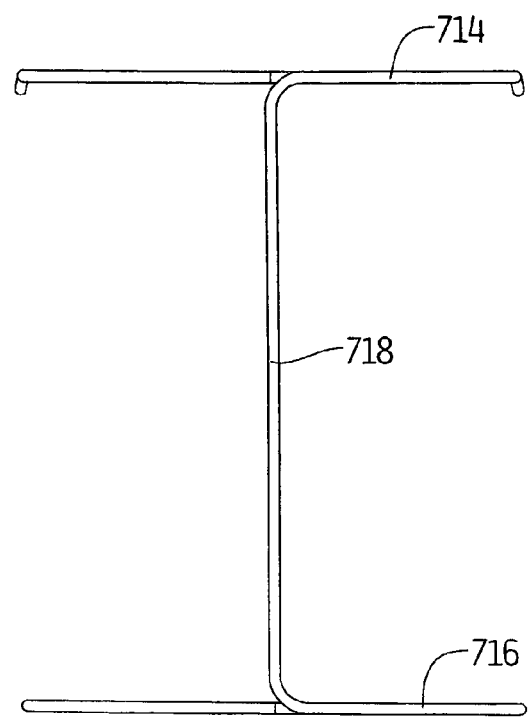

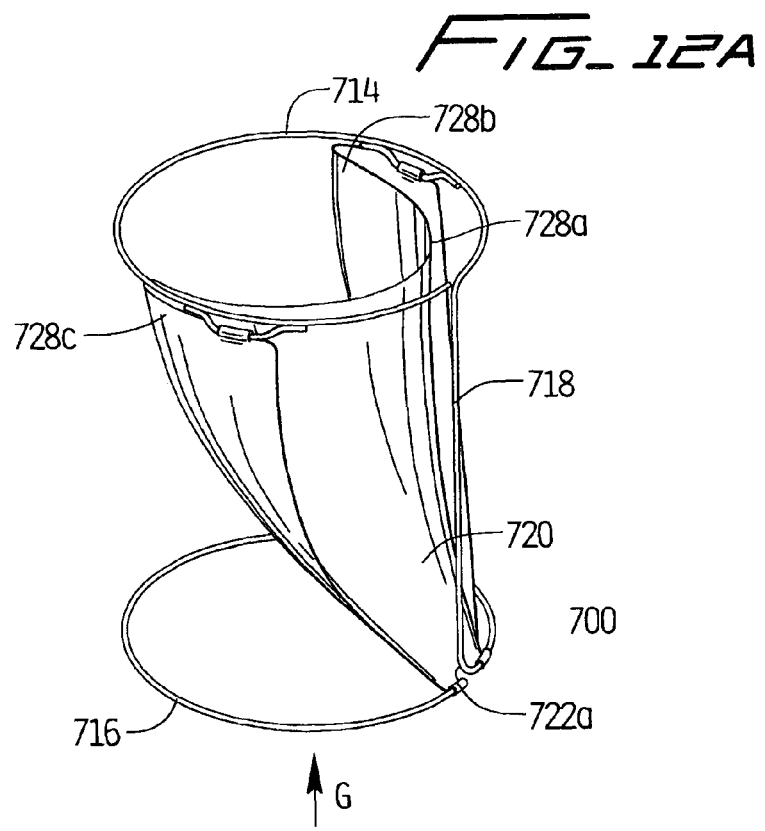
FIG_12A
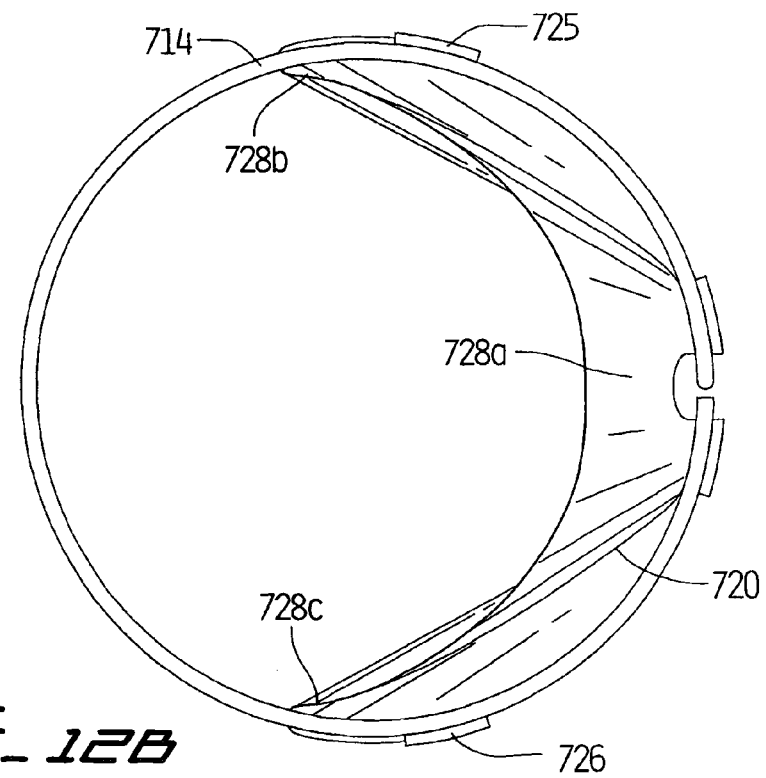
FIG_12B

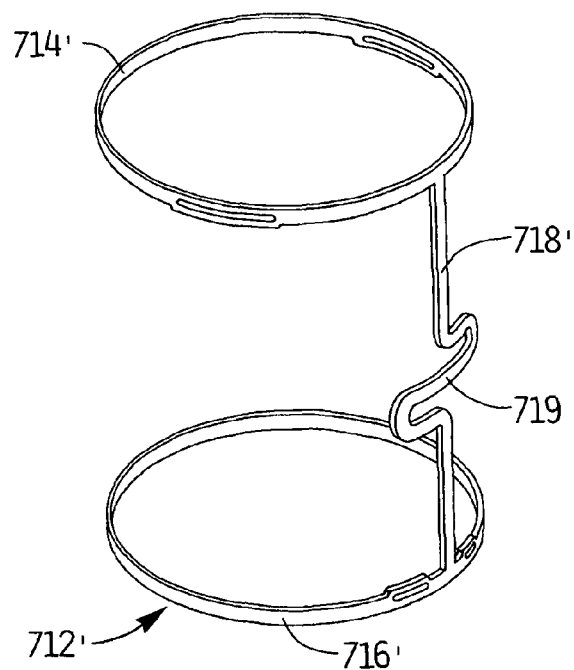
FIG_12C
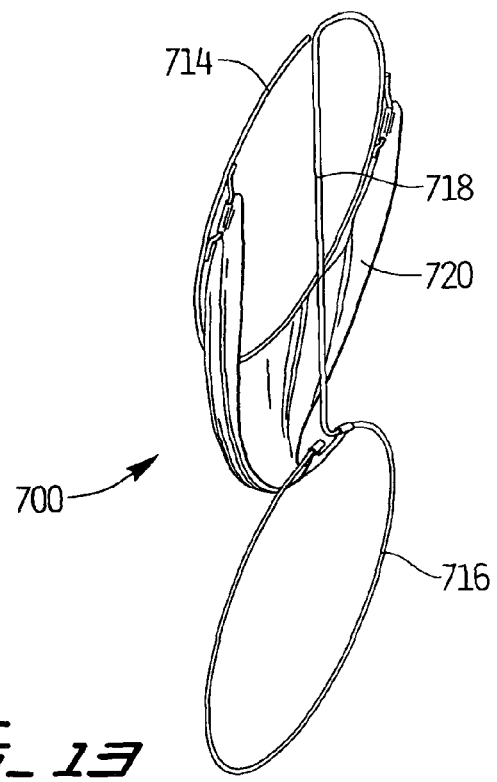
FIG_13

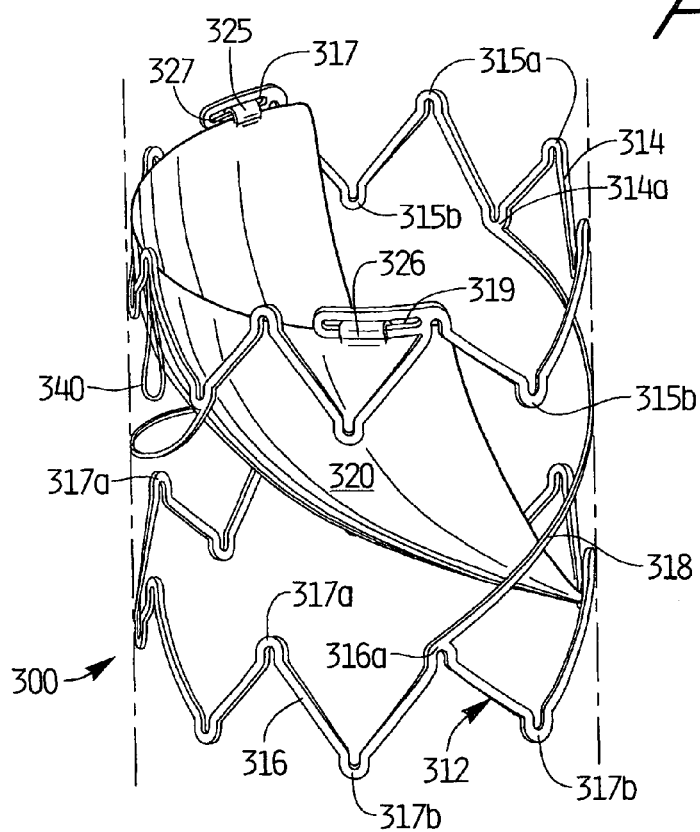
FIG_14A
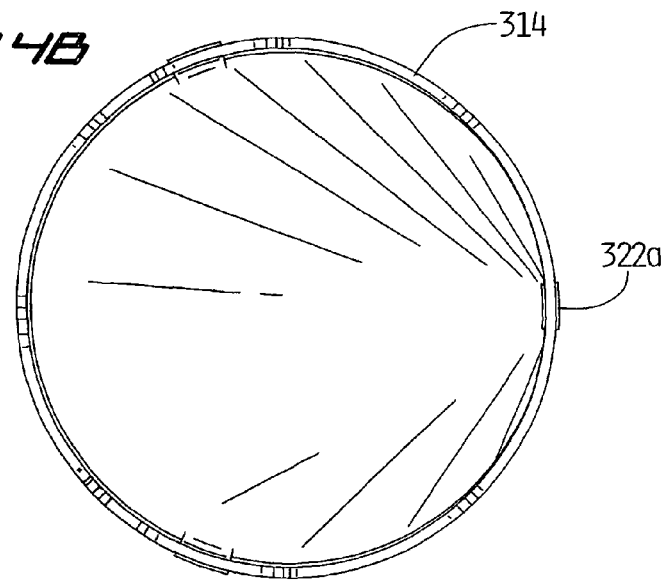
FIG_14B

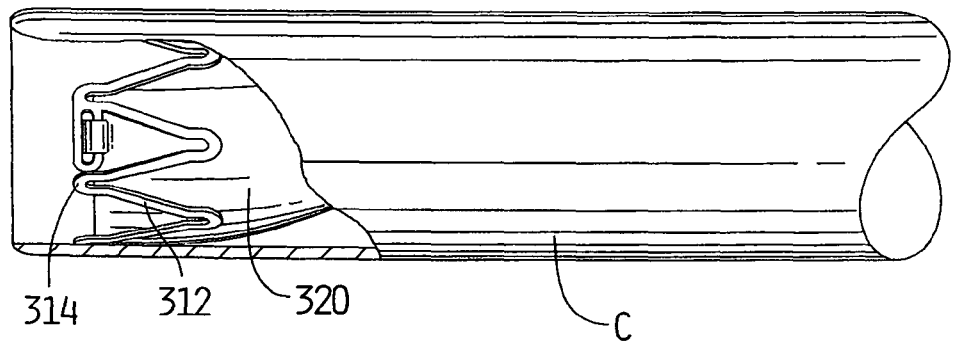
FIG_16
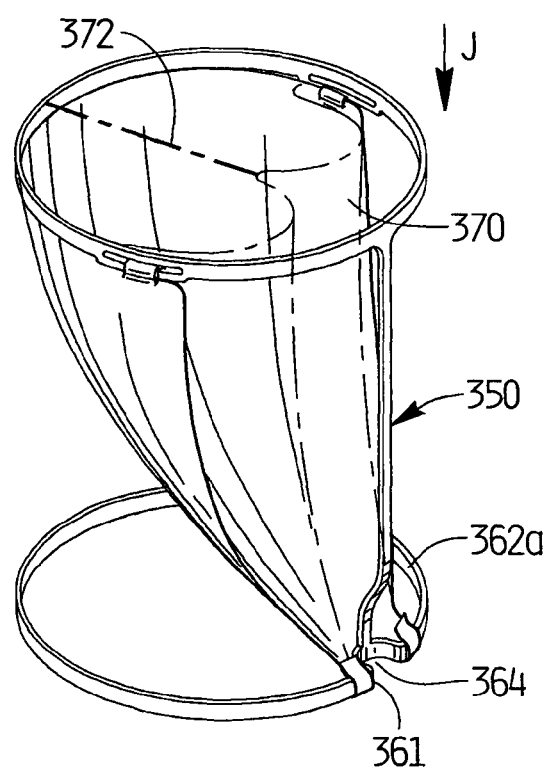
FIG_17

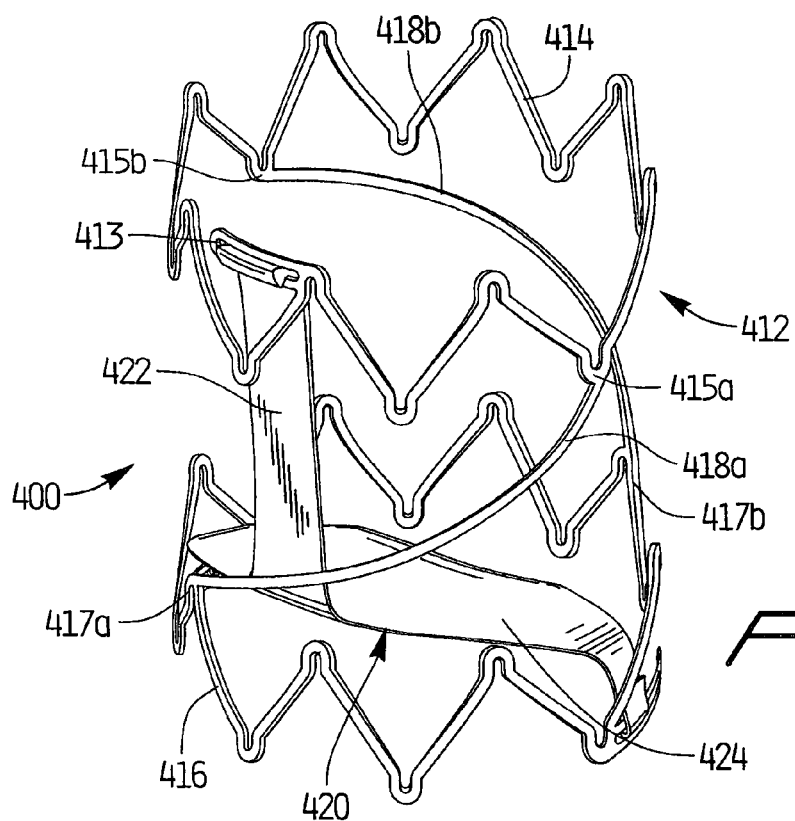
FIG_18A
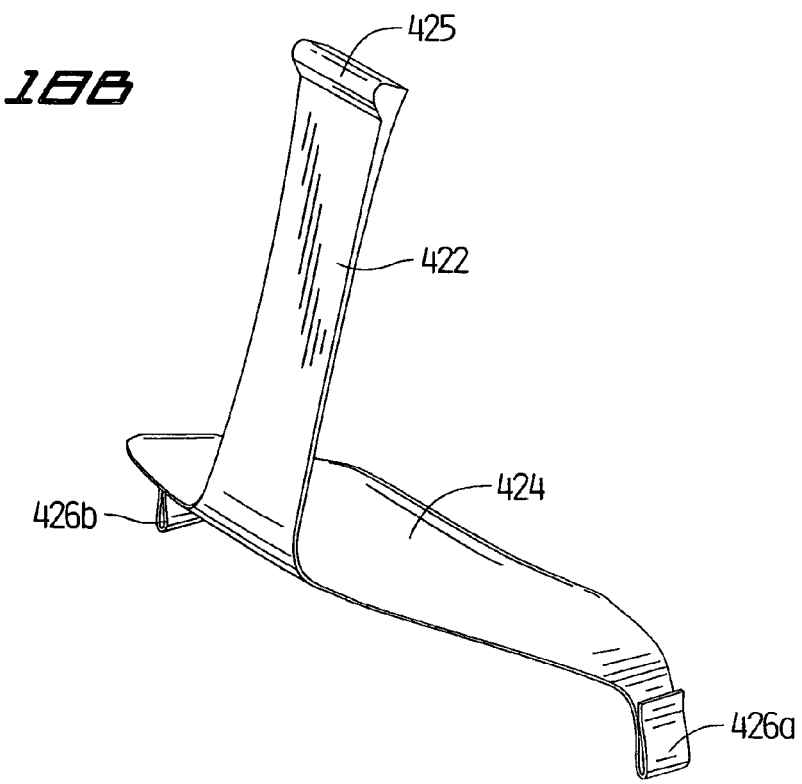
FIG_18B

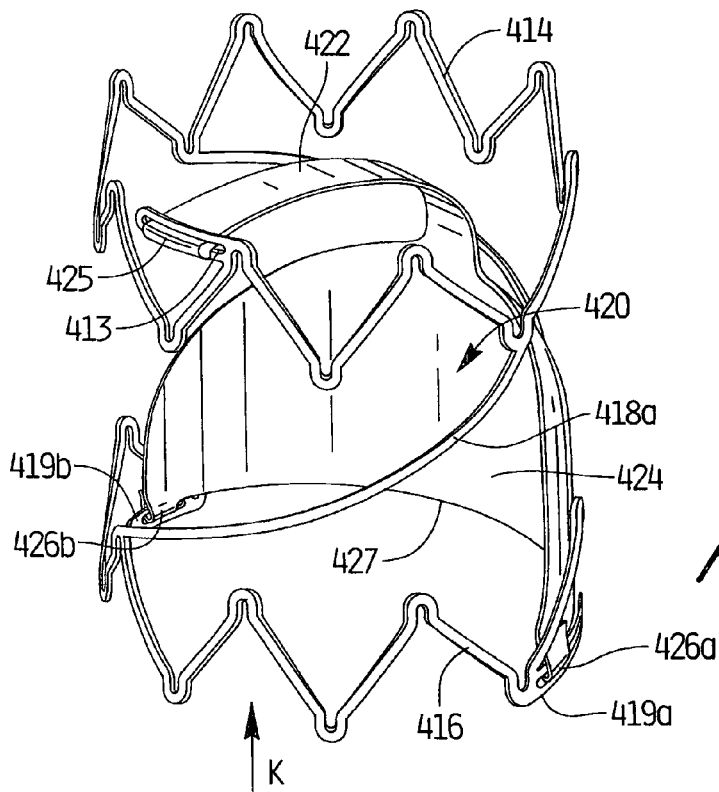
FIG_19A
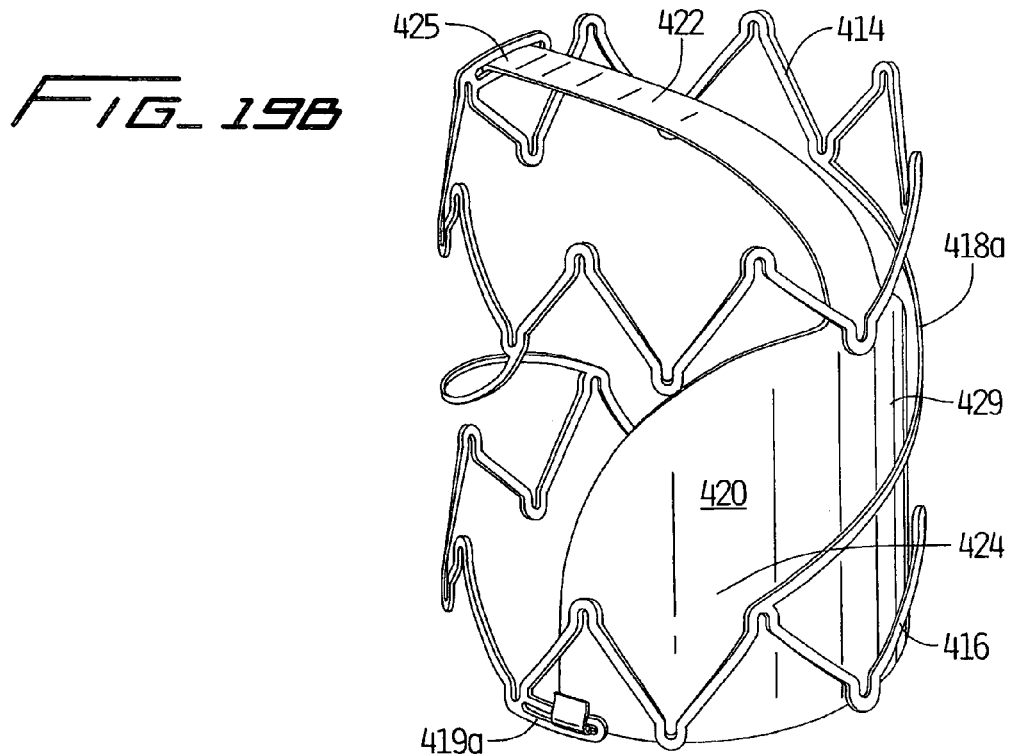
FIG_19B

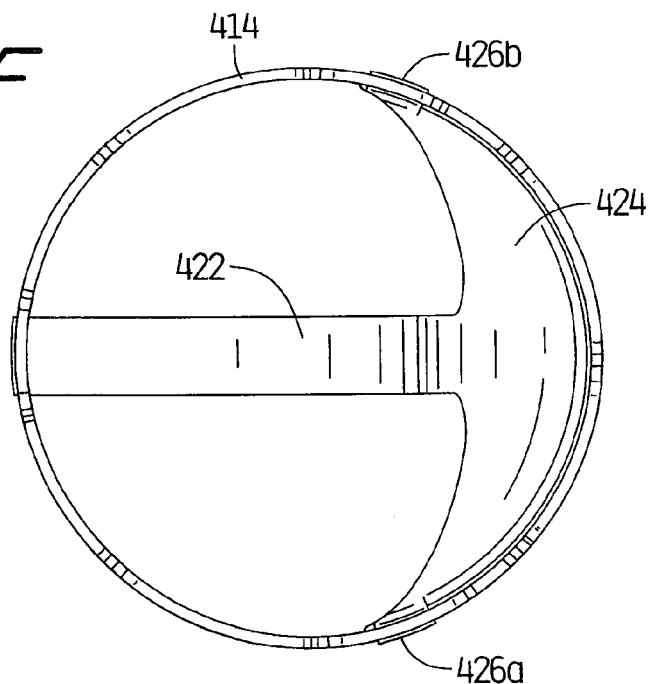
FIG_19C
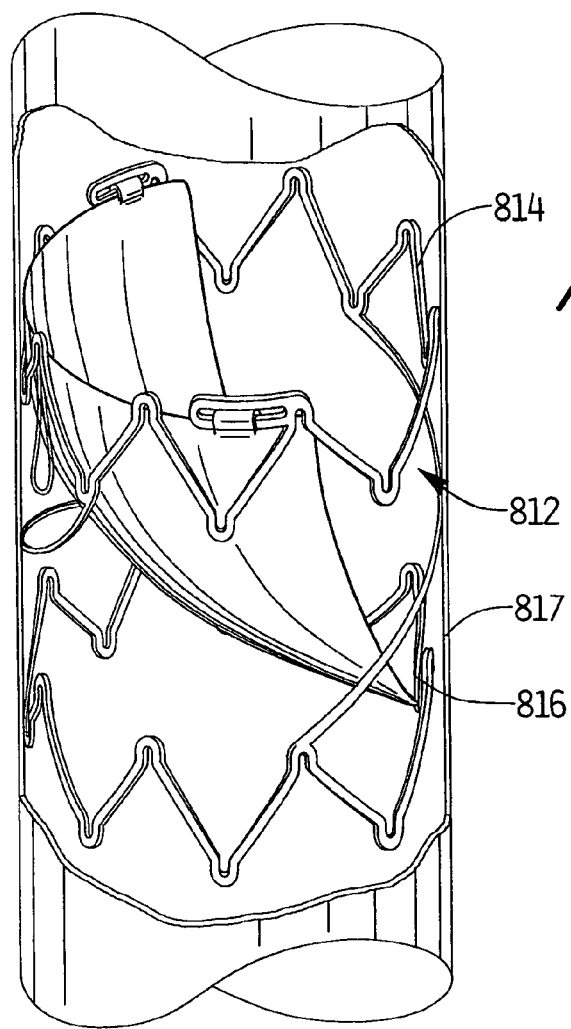
FIG_21

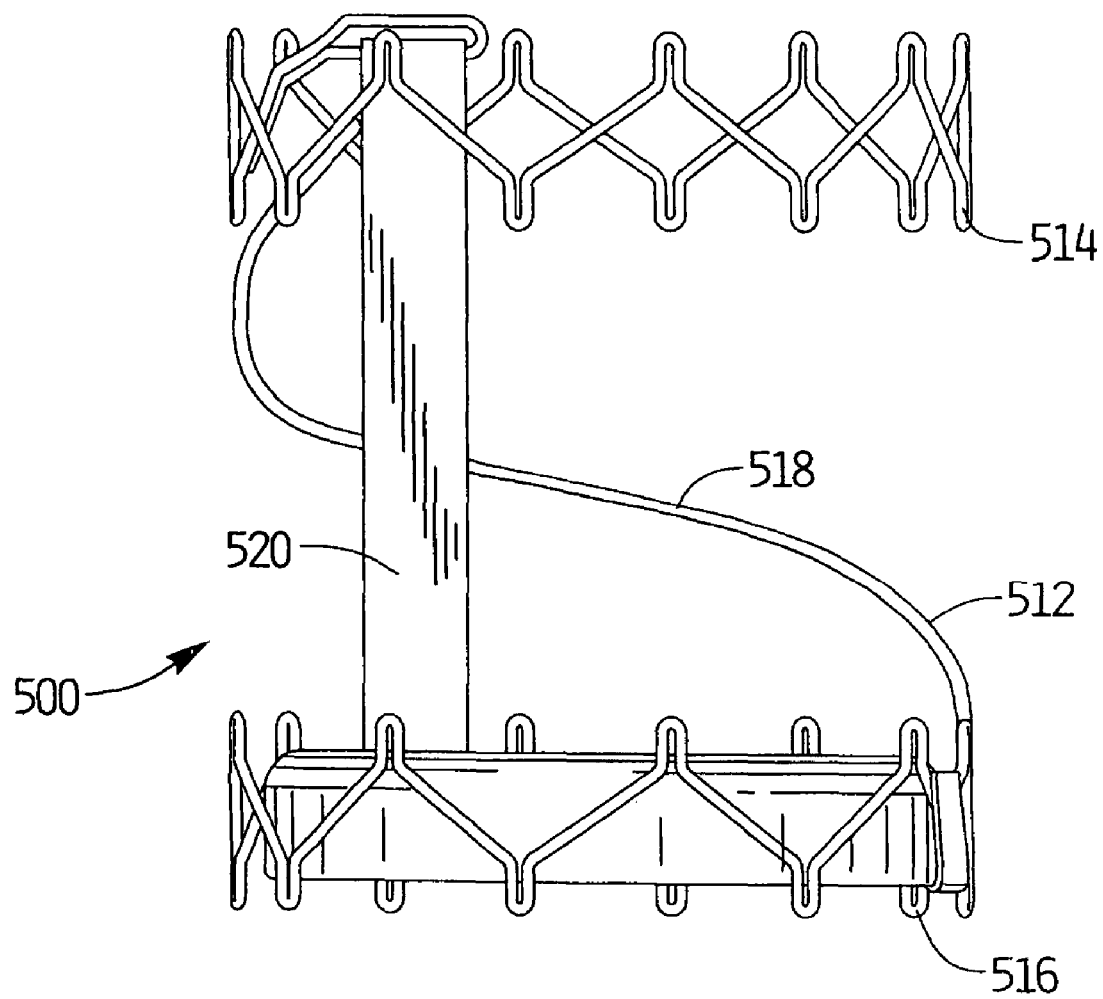

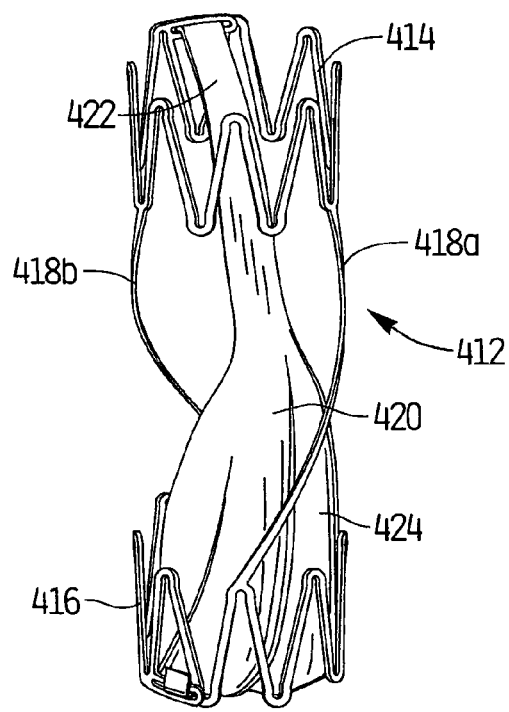
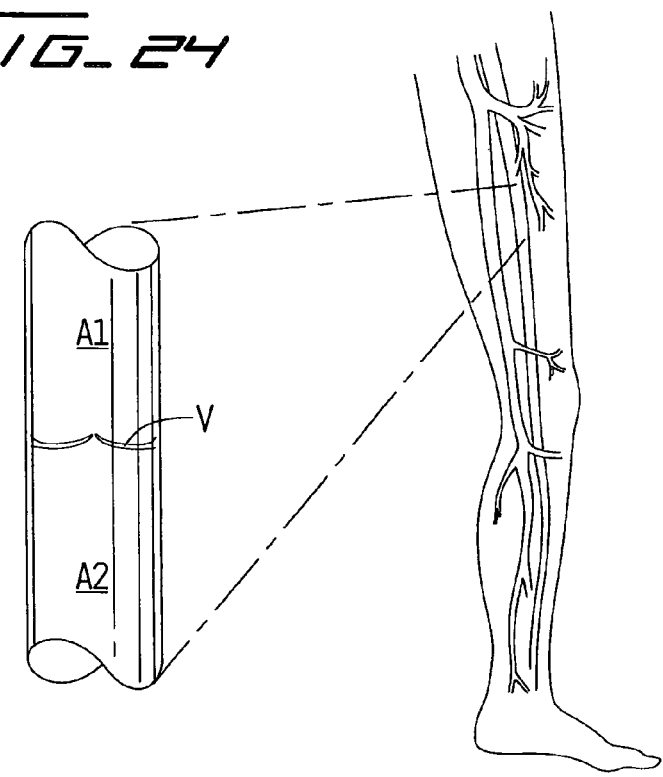

DEVICE FOR REGULATING BLOOD FLOW

BACKGROUND OF THE INVENTION

This application claims priority from provisional application Ser. Nos. 60/808,406, filed May 25, 2006 and 60/809,483, filed May 31, 2006, the entire contents of which are incorporated herein by reference.

1. Field of the Invention

The subject invention is directed to a device for regulating blood flow in the venous system, and more particularly, to an implantable valve device for regulating the flow of blood through a blood vessel.

2. Description of Related Art

The blood system, and in particular the venous blood system of the legs and arms is provided with valves that are uniquely located in a manner so as to ensure that blood will not flow back upstream in the direction from which it has been pumped from the heart. In the arms and legs, there is a deep venous system and a surface venous system. Due to various causes, thrombosis can occur in the deep venous system. Blood thinning can alleviate this problem. However, valves do not effectively close and often leak when the blood in thinned. This can cause increased venous blood pressure in the direction of the ankles, which can lead to a variety of problems including varicose veins and open leg. Complaints of this type are wide spread among those who spend prolonged periods of time in a standing position, for instance, surgeons.

The surface venous system of the leg is relatively weaker than the deep venous system, and it has the tendency to spontaneously widen. This widening prevents the valves from functioning effectively and can lead to varicose veins, which are both unattractive and painful. Major surgery is often required to treat these blood vessel problems. For example, varicose veins are treated by either closing off the vein, which leads to a reduced blood flow capacity and increased pressure on surrounding blood vessels to ensure blood supply, or by completely removing the varicose veins, which leads to the same problem. The subject invention is directed to a device for obviating problems of this type.

SUMMARY OF THE INVENTION

More particularly, the subject invention is directed to a new and useful implantable valving device for mechanically regulating blood flow through a blood vessel. The device includes, among other things an elongated support dimensioned and configured to be implanted in a blood vessel. The support includes axially spaced apart first and second support portions and at least one linking member connecting the axially spaced apart portions to one another. A valve membrane is supported between the axially spaced apart portions of the support and adapted for movement between a first position in which blood flow through the support is permitted and a second position in which blood flow through the support is inhibited. In the second position, the valve membrane has a convex outer surface and in the first position the valve membrane has a wavy shape.

In one embodiment, the first and second support portions are substantially annular and have a wavy configuration.

In one embodiment, the device includes a suture extending between the first support portion and the valve membrane. Preferably, the suture is attached to a region of the membrane spaced from its edges to limit movement of the valve towards the first position. The membrane can include first and second flaps formed by a folded edge for attachment to the support portions.

In one embodiment, the second portion of the support includes an indent or a dent to form a gap between the support (and membrane) and vessel wall to enable backflow of blood when the membrane is in the second position.

The support can be formed from a laser cut tube. Alternatively, it can be formed from at least one wire.

The present invention also provides an implantable device for regulating blood flow through a blood vessel comprising an elongated support dimensioned and configured to be implanted in a blood vessel. The support includes first and second axially spaced apart portions and a curved linking member joining the first and second portions at about 90 degrees apart. A valve membrane is supported between the axially spaced apart portions and adapted for movement between a first position in which blood flow through the support is permitted and a second position in which blood flow through the support is inhibited.

In one embodiment, the membrane includes a first body portion and a second narrower neck portion, wherein the first body portion is attached to the second support portion and the neck portion is attached to the first support portion. The neck portion can include a first flap formed by a folded edge of the membrane and the body portion can include a second flap formed by a folded edge for attachment to the support. Preferably, the narrower neck portion has a length at least equal to the radius of the first support portion and preferably extends upwardly and outwardly in an arc extending away from the body portion.

In one embodiment the first and second portions of the support form substantially ring-like members wherein the support is formed from two wires, the first wire forming part of the first substantially ring like member and one linking member and the second wire forming part of the second substantially ring-like member and another linking member.

BRIEF DESCRIPTION OF THE DRAWINGS

So that those skilled in the art to which the subject invention appertains will readily understand how to make and use the apparatus of subject invention without undue experimentation, preferred embodiments thereof will be described in detail hereinbelow with reference to certain figures, wherein:

FIG. 1 is a perspective view of the frame of a flow-regulating device constructed in accordance with one embodiment of the subject invention;

FIG. 2 is a plan view of a membrane employed with the frame of FIG. 1;

FIG. 3 is a schematic perspective view of the flow-regulating device of the subject invention, wherein the frame is simplified to illustrate the position of the membrane to permit blood flow through a vessel;

FIG. 4 is a schematic perspective view of the flow-regulating device of the subject invention as in FIG. 3, with the membrane oriented to block the flow of blood through a vessel;

FIG. 5 is a perspective view of another flow-regulating device constructed in accordance with another embodiment of the subject invention with the membrane oriented to block blood flow through a vessel;

FIG. 6 is a perspective view as in FIG. 5, with the membrane oriented to permit blood flow through a vessel;

FIG. 7 is a perspective view of a flow-regulating device constructed in accordance with yet another embodiment of the subject invention with the frame in a collapsed condition;

FIG. 8 is a perspective view of the device shown in FIG. 7, with the frame expanded into an open position;

FIG. 9 is a perspective view of the device of FIG. 7, shown with a balloon catheter prior to deployment in a blood vessel;

FIG. 10 is a perspective view of the device of FIG. 7, shown with a balloon catheter inflated to expand the device into a deployed condition within a blood vessel FIG. 11A is a perspective view of an alternate embodiment of the flow regulating device of the subject invention shown in the closed position to block blood flow;

FIG. 11B is a perspective view of the flow regulating device of FIG. 11A with the support removed for clarity;

FIG. 11C is a top view of the flow regulating device of FIG. 11A;

FIG. 11D is a side view of the support of FIG. 11A with the membrane removed for clarity;

FIG. 12A is a perspective view of the flow regulating device of FIG. 11 shown in the open position to permit blood flow;

FIG. 12B is a top view of the flow regulating device of FIG. 12A;

FIG. 12C is an alternate embodiment of the support of FIG. 11A;

FIG. 13 is a perspective view of the flow regulating device of FIG. 11 in the collapsed position for delivery;

FIG. 14A is a perspective view of another alternate embodiment of the flow regulating device of the present invention shown in the closed position to block blood flow;

FIG. 14B is a top view of the flow regulating device of FIG. 14A;

FIG. 16 is a side view of the flow regulating device shown in the collapsed position within a delivery catheter with a portion of the catheter broken away;

FIG. 17 is a perspective view of an alternate embodiment of the flow regulating device of FIG. 14 having a dent formed in the bottom ring, the device shown in the closed position;

FIG. 18A is a perspective view of yet another alternate embodiment of the flow regulating device of the present invention having a wavy ring support shown in the closed position, the top and bottom rings joined by two 90 degree curved connectors;

FIG. 18B is a perspective view of the flow regulating device of FIG. 18A with the support removed for clarity;

FIGS. 19A and 19B are perspective views from different sides of the flow regulating device of FIG. 18 shown in the open position;

FIG. 19C is a top view of the flow regulating device of FIG. 19A;

FIG. 20 is a perspective view of the flow regulating device of FIG. 18 in the collapsed position for delivery;

FIG. 21 is a perspective view of an alternate embodiment of the flow regulating device, wherein a dent is formed in the bottom ring of the support;

FIG. 22 is a perspective view of another alternate embodiment of the flow regulating device wherein the rings are joined by a 180 degree twisted connector;

FIG. 24 is a drawing of the anatomy of the patient showing two examples of locations of placement of the flow regulating device.

ENABLING DESCRIPTION OF PREFERRED EMBODIMENTS

Figure 15A:
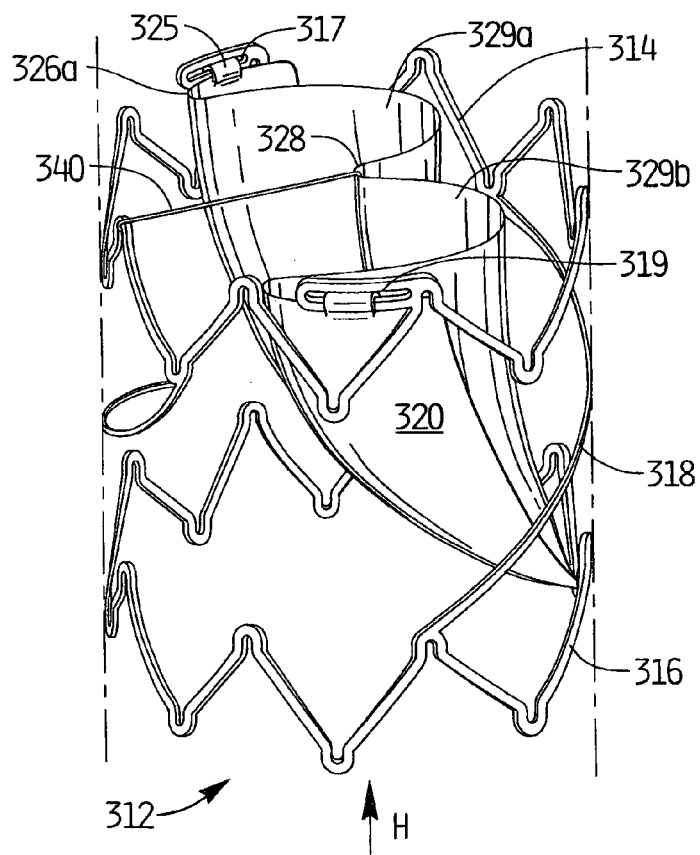
FIG. 15A is a perspective view of the flow regulating device of FIG. 14A shown in the open position to permit blood flow.

Referring now to the drawings wherein like reference numerals identify similar or like components throughout the several views, there is illustrated in FIG. 1, a flow regulating device constructed in accordance with a preferred embodiment of the subject invention, and designated generally by reference numeral 10. Regulating device 10 includes an elongated frame 12 that consists of upper and lower crown-shaped or wave-like rings 14 and 16. That is, each ring has connecting V-shapes as shown. These rings 14, 16 are preferably larger in diameter than the host vein in their expanded placement (deployed) configuration, to ensure that the device remains in a desired position and orientation after implantation. For example, the diameter of the rings may be about 1.15% to about 1.30% larger than the diameter of the intended host vein, and more preferably about 1.20% to about 1.25% larger, although clearly other sizes are contemplated.

Rings 14 and 16 are connected to one another by at least one connective or linking member in the form of a bar or wire 18. For ease of illustration, only one connective wire 18 is shown in FIG. 1. Bar or wire 18 is curved and adapted and configured to follow the circumference of the host vessel. Preferably, the bar or wire 18 is attached to the opposed rings 14 and 16 of frame 12 at locations that are about 180° apart from one another, as shown. This gives frame 12 an inherent flexibility and enables it to move with the natural movements (e.g., peristaltic) of the vein and to accommodate movement of the leg.

Due to the crown-shape of the rings 14 and 16, the device 10 can be reduced to approximately ⅕ of the final implanted diameter and could be introduced into a blood vessel through a relatively small delivery device. For example, a device having a working diameter of 6F to 8F could be used.

As shown in FIGS. 3 and 4, wherein the connective rod(s) 18 are not shown and the rings 14, 16 are simplified for ease of illustration, device 10 includes a valve member 20 that is operatively associated with frame 12 for regulating the flow of blood through a vessel by moving between open and closed positions. Valve member 20 (as well as the other members disclosed herein) is preferably formed from a sheet of ultra thin membrane material such as a non-expandable PTFE material or the like. It is envisioned that the membranes disclosed herein could be bonded or otherwise coated with an anti-clotting or anti-coagulant agent such as Heparin and/or an anti-proliferative coating to retard the body's desire to reject the implant.

As best seen in FIG. 2, valve membrane 20 has a narrow elongated neck portion 22 for attachment to the upper ring 14 of frame 12 and a wide body portion 24 for attachment to the lower ring 16 of frame 12. The narrow neck portion 22 as shown extends across the diameter of the device, and preferably has a length greater than a radius of the device (ring) and slightly less than the diameter of the ring. The attachment locations (22a of neck portion 22 and 24a, 24b of body portion 24) of the membrane 20 on each ring are preferably approximately 180° degrees from one another so that the body portion 24 of the membrane 20 will extend substantially if not entirely across the expanse of frame in the closed position shown in FIG. 4. Note the membrane could be attached to ring 16 along its curved perimeter or attached at specific points, e.g. 24a, 24b, or at additional points.

Referring to FIG. 3, blood flowing through the blood vessel 30 in the downstream direction indicted by arrow "A" will act against the valve membrane 20 in such a manner so as to push the wide body portion 24 of the membrane 20 against the wall of the blood vessel 30. At such a time, blood will flow freely through the frame 12, impeded only incidentally by the narrow neck portion 22 of membrane 20 extending across the device.

Referring to FIG. 4, blood flowing through the blood vessel 30 in the upstream direction indicated by arrow "B" will act against the valve membrane 20 in such a manner so as to push the wide body portion 24 in a direction as shown, substantially if not entirely closing off blood flow through the blood vessel 30. Due to the length of the narrow part 22 of the valve membrane 20, the wide body portion 24 will close at a relatively steep angle (e.g., 30°). This is important because the steeper the closure angle, the less force required to push the valve membrane back to an open position with the natural blood pressure.

Referring now to FIG. 5, to minimize the number and complexity of implantable components, an implantable device 100 is provided that includes a frame 112 having two axially spaced part substantially circular rings 114, 116 and a connecting bar 118, with an ultra thin, generally triangular shaped membrane 120 operatively associated therewith. As shown, each of the rings 114, 116 is positioned at an angle, preferably obtuse as shown, to the connecting bar 118. The lower apex of the triangular membrane 120 is attached to the lower ring portion 116 of frame 112 (attachment region 121a), and the upper apices of the triangular membrane 120 are attached to the upper ring portion 114 of frame 112 at diametrically opposed positions (attachment regions 122a, 122b). Preferably, the upper portion of the membrane 120 is loosely attached to the upper ring portion 114, allowing it to slide down the ring during insertion. The lower portion of the membrane 120 is attached to the lower ring portion 116 in the same general area as the connecting rod 118. The membrane has a curved or convex outer surface 119 in the flow blocking position of FIG. 5 and a curved or convex outer surface 117 facing in the opposite direction (radially) in the blood flow position of FIG. 6 (see arrow D).

It is envisioned that the frame 112 (and frame 12) is made from a shape-memory or super-elastic material such as Nitinol or a similar material, so as to enable the collapse and recovery of the rings during implantation in blood vessel 30. The ultra thin membrane 120 is preferably made from a material such as PTFE, and may be provided with an anti-clotting drug and/or an anti-proliferative agent.

It is also envisioned that valve membrane 120 can have a small slit or hole 126 adjacent the lower apex of the membrane near the connection with lower ring portion 116 to allow some of the blood trapped behind to flow back through the membrane. This will reduce the likelihood of clotting.

FIGS. 11-13 illustrate a variation of the flow regulating device of FIG. 5. In FIG. 11A, device 700 has a support 712 having first and second substantially annular members forming ring-like members 714, 716 which are substantially perpendicular to the direction of blood flow and substantially perpendicular to the linking member 718 which joins the two ring members 714, 716. The linking member 718 as shown in this embodiment is substantially straight but could alternatively be curved. The support 712, as best shown in FIG. 11D, is formed from a single wire which loops around in almost a complete 360 degree circle to form ring member 714, extends perpendicular to a diameter of the ring 714 to form linking member 718, and then loops around in almost a complete 360 degree circle to form ring 716.

A substantially triangular membrane 720 is mounted to the support 712. The lower region of the membrane 720 has two adjacent flaps 722a formed by a fold at the bottom edge 724 for attachment to the lower ring 716 as the wire extends through the flaps as shown in FIGS. 11A and 11B. The upper region of the membrane 720 has two flaps 725, 726 spaced about 180 degrees apart and formed by two folds in the edge 727 of the membrane 720. The flaps 725, 726 receive a portion 717, 719, respectively, of the wire support 712 (see FIG. 11C). Flaps 722a receive portion 729 of wire support 712 therethrough. Gap 723 allows for the backflow of blood when the membrane is in the closed position.

In the open position shown in FIG. 11A, the convex outer surface 731 of membrane 720 angles across the support 712 to block blood flow. When blood flows in the direction of arrow G, it will act against the membrane 720 to move membrane 720 to the open position of FIG. 12A. In this position, with the flaps 722a, 725 and 726 remaining fixed with respect to the support 720, the membrane 720 folds on itself to form a wavy substantially W-shape as shown in FIGS. 12A and 12B. The positioning of the flaps limits the folding of the membrane 120 so it remains spaced from the vessel wall. As seen, the W-shape creates an outwardly curved surface 728a facing in a first direction, and two curved surfaces 728b, 728c facing in a second opposite direction. Backflow of blood returns the membrane to the position of FIG. 11A.

The collapsed position of flow regulating device 700 is shown in FIG. 13 with the ring portions 714, 716 collapsing to a more elongated (straighter configuration) to reduce the profile for insertion of the device 700. As shown, top ring 714 bends toward the linking member 718 while bottom ring 716 bends away and towards linear alignment with linking member 718.

In the alternate embodiment of FIG. 12C, the support 712' is similar to support 712 of FIG. 12 except first and second rings 714', 716' are joined by a linking member 718' which has a sinuous shape intermediate portion 719 which increases flexibility.

FIGS. 14-15 illustrate an alternate embodiment of the flow regulating device, designated by generally by reference numeral 300, wherein the support 312 has annular rings 314 and 316 of crown or wavy configuration and a suture 340 extending from the support 312 to the membrane 320.

More specifically, support 312 can be formed from a cut tube, preferably laser cut, into the configuration shown wherein the annular ring-like members 314 and 316 each have a crown shaped formed by connected V-shaped members. The alternating apices 315a, 315b and 317a, 317b of the V-shapes are rounded. (For clarity, not all the apices are labelled.) A curved linking member 318 joining the first and second rings 314, 316 preferably extends through a curve of about 90 degrees. That is, it extends from ring 314 at a region 314a which is spaced about 90 degrees apart from the region 316a where it extends from ring 316. Although a single linking member is shown, as with the other embodiments disclosed herein, two or more linking members could be provided. Also, as with the other embodiments disclosed herein, the linking members could be spaced apart at regions different than 90 degrees apart, such as 180 degrees, 120 degrees, etc.

Membrane 320 includes flaps 325, 326 in the upper region, spaced about 180 degrees apart and formed by folds in the edge 327 of the membrane 320. The flaps 325, 326 extend through a slot 317, 319, respectively, formed in the ring portions 314, 312. The lower region of the substantially triangular membrane 320 has a single flap 322a (although alternatively multiple flaps could be formed). Flap 322a is formed by a fold at the bottom edge 324 for attachment by extending through a slot formed in the lower ring 316.

A flexible material 340, shown in the form of a suture, extends from a middle region of the membrane 320 to the upper ring 314. Preferably it loops through a slot in the ring at one end and is stitched to the membrane at the other end. However, it is also contemplated that the flexible material could alternately be integral with the membrane 320, i.e. formed of the same material. Thus, in this version, the flexible material would be in the form of a strap attached at its other end to the ring and would function in the same manner as suture 340 described herein.

Figure 15B:
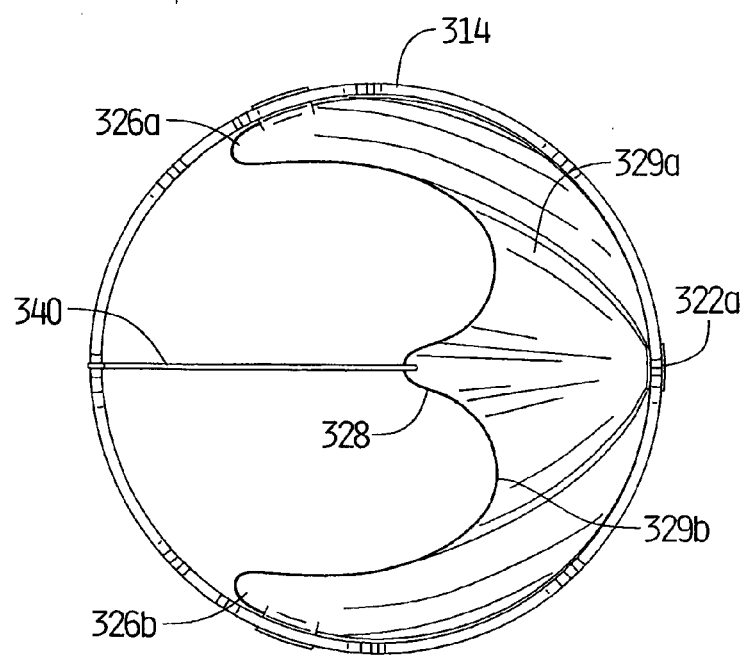
FIG. 15B is a top view of the flow regulating device of FIG. 15A.

Suture 340 is shown in the untensioned position of FIG. 14a, corresponding the closed (blocking) position of the membrane 320. When blood flows in the direction of arrow H of FIG. 15A, the blood acts on membrane 320 to move membrane 320 toward the opposing side of the support 312. However, the suture 340 is tensioned as shown in FIG. 15A to limit the movement of the membrane 320. This keeps the membrane 320 away from the edge of the support 312 and away from the vessel wall. It also maintains the wavy configuration of the membrane. As shown in FIGS. 15A and 15B, the wavy shape is formed by the inwardly curved surface 328 facing in a first direction, two curved surfaces 329a, 329b facing in a second opposite direction, and two curved surface 326a, 326b facing in the first direction, as the flaps are held in position through the slots of the support. Note the length of the suture can be varied to adjust the extent of movement of the membrane.

The collapsed configuration of the flow regulating device 300 is shown in FIG. 16 positioned in a delivery catheter C.

FIG. 17 illustrates an alternate embodiment of the flow regulating device, shown for ease of illustration with the ring-like support of FIG. 11A but it is also contemplated that the crown-shaped support could be utilized. The support 350 has an indent formed in the lower ring 362a to create a gap 364. That is, a dent is formed in the ring such that a portion of the circumference extends toward a center of the ring-like support to create the gap. This gap enables the back flow of a limited amount of blood in the direction of arrow J between the device 300 and the vessel wall when the membrane 370 is in the closed position to reduce the likelihood of clotting. The device has a suture 372 functioning in the same manner as suture 340 of FIG. 15. As described with respect to FIG. 15, other flexible material besides suture 372 could be utilized.

Note this indent can be utilized with any of the embodiments described herein to enable back flow of blood. For example, in FIG. 21 lower ring 816 of frame 812 has a dent or indentation so it is spaced from the vessel wall. That is, as can be seen in FIG. 21, upper ring 814 fills the diameter of the vessel wall while the lower ring configuration forms a gap 817 with the vessel wall to allow back flow of blood.

FIGS. 18-20 illustrate an alternate embodiment of the flow regulating device, designated generally by reference numeral 400. Support 412 is similar to support 312 of FIG. 14A in that it has two annular ring portions 414, 416 which are crown shaped. However, support 412 has two linking members 418a, 418b, each of which extends through an approximate 90 degree curve (twist). That is, region 415a of ring 414 from which linking member 418a extends, is about 90 degrees out of phase from region 417a of ring 416, from which the other end of linking ember 418a extends. Region 415b of ring 414 from which linking member 418b extends, is about 90 degrees out of phase from region 417b of ring 416, from which the other end of linking ember 418a extends.

Membrane 420 has a elongated narrow neck portion 422 and a wider body portion 424. The narrow neck portion 422 as shown extends across the diameter of the device in the open position, and preferably has a length greater than a radius of the device (ring) and less than the diameter of the ring.

Neck portion 422 is attached to upper ring 414 by engagement of flap 425 with a portion of the ring extending therethrough as it extends through slot 413. The body portion 424 includes flaps 426a, 426b in the lower region, preferably spaced about 180 degrees apart, and formed by two folds in the edge 427 of the membrane 320. The flaps 426a, 426b extend through slots 419a, 419b respectively, formed in the ring portion 416.

As shown in FIG. 18A in the flow blocking position, body portion 424 extends at a slight angle to a diameter of the ring 416 and neck portion 422 extends substantially perpendicular to the ring 414. When blood flows in the direction of arrow K as shown in FIG. 19A, the blood acts on membrane 420 to move membrane 420 to the flow permitting position wherein the body portion 424 is moved toward an edge of the support 412 and the neck portion 42 flips so that it extends in an arc upwardly from the body portion and across a portion of the support 412. In this position, convex surface 429 is adjacent the edge of the support 412, but preferably spaced from the edge and the vessel wall. The length of the neck portion 422 limits the extent of travel of the membrane 420 and can be adjusted in manufacture accordingly to vary the extent of movement of the membrane 420.

In the collapsed position for delivery shown in FIG. 20, the diameter of the rings 414, 416 is reduced to thereby reduce the profile.

As noted above, the support is preferably composed of a laser cut tube. However, it is also contemplated that alternatively the support can be formed from wire(s). As shown for example in FIG. 22, wire 512 of device 500 is formed into two crown ring shapes 514, 516. Rings 514 and 516 are formed by a 180 degree linking member 518. Membrane 520 is similar to membrane 420.

Figure 23:
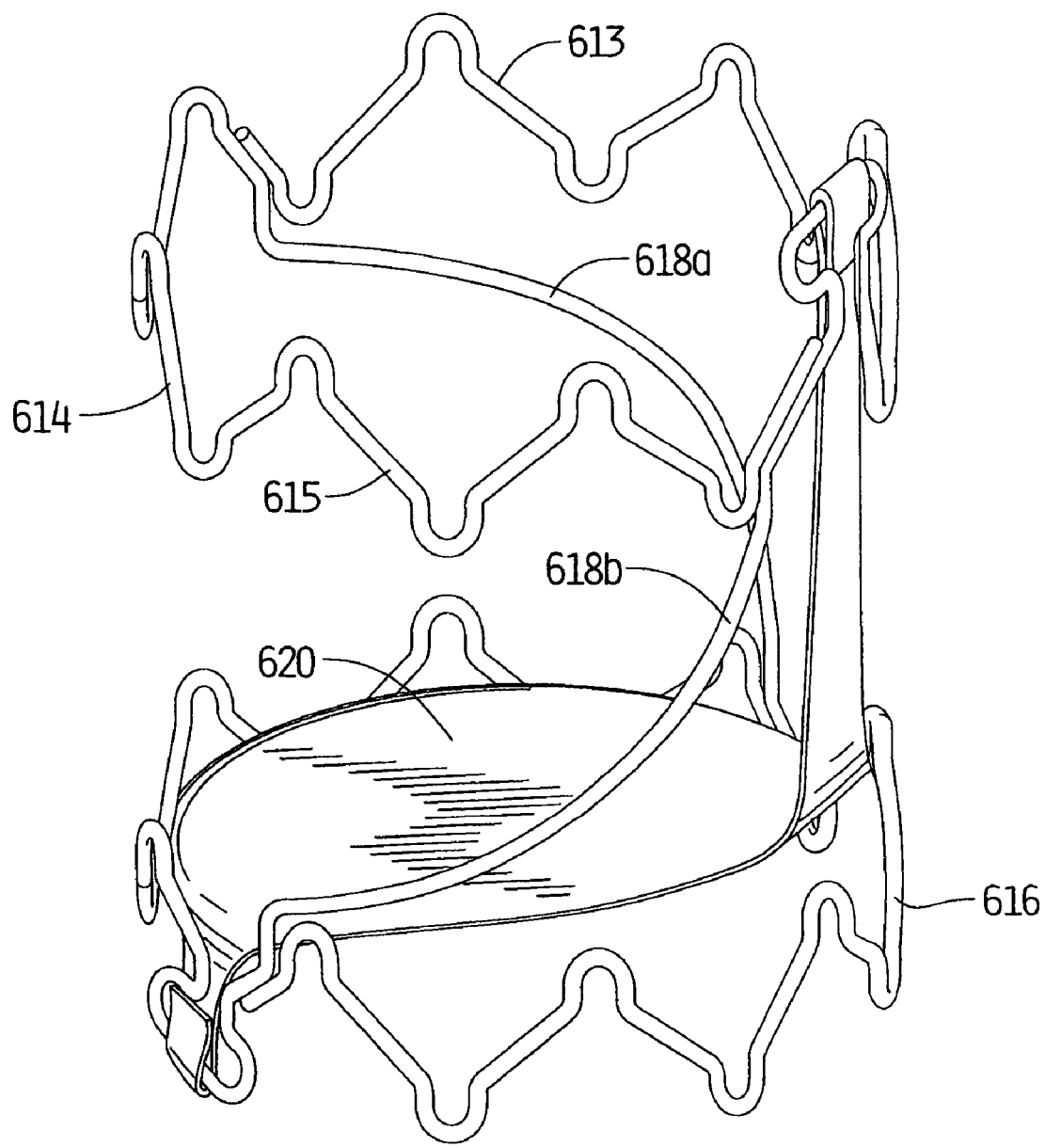
FIG. 23 is a perspective view of another alternate embodiment of the flow regulating device of the present invention having a support formed by wires.

FIG. 23 is similar to FIG. 22, however, the rings 614 and 616 are connected by two linking members 618a and 618b, each extending through a 90 degree curve. As shown, the first wire 613 forms about half of ring 614, linking member 618b and about half of ring 616. Wire 615 forms the other section (other half) of ring 614, linking member 618a, and the other section of ring 616. The membrane 620 is substantially identical to membrane 420 of the embodiment of FIG. 19.

One example of the location of placement of the flow regulating device in a patient's leg is shown in FIG. 24 with areas A1 and A2 showing possible placement sites of the device, e.g. upstream or downstream of the native valve V.

Referring now to FIGS. 7 through 10, there is illustrated another embodiment of the implantable device of the subject invention, which is designated generally by reference numeral 200. Device 200 includes a frame 212 having opposed flexible straps 214, 216 and a connecting structure 218. Straps 214 and 216 are preferably formed from a shape memory material that is normally biased into a coiled or closed configuration, shown for example in FIG. 7. A generally triangular membrane 220 is attached to frame 212 in a manner similar to the way in which membrane 120 is attached to frame 112. The rings 214, 216 of frame 212 are adapted and configured for securement in an expanded or open position, shown in FIG. 8, through the interaction of a locking tangs 217 and apertures 215.

As illustrated in FIGS. 9 and 10, device 200 is implanted in a blood vessel using a balloon catheter 240. More particularly, rings 214 and 216 are moved from a closed position to an expanded position by inflating balloon 242. Upon expansion, to a desired position, tangs 217 engage apertures 215 to lock the rings 214 and 216 in a desired position. The balloon 242 is then deflated and the catheter 240 is removed from the blood vessel so the device 200 can regulate the flow of blood through the vessel, in the manner described previously with respect to device 100.

In the embodiments disclosed herein showing substantially circular rings, it should be understood that the rings can be shaped to have a size larger than the diameter of the vessel and therefore, depending on the size of the vessel, may not assume a circular shape but have an oval shape pressing against the vessel wall toward a circular configuration.

While the above description contains many specifics, those specifics should not be construed as limitations on the scope of the disclosure, but merely as exemplifications of preferred embodiments thereof. For example, the various supports disclosed herein could have indents or dents such that a portion of the circumference extends toward the center of the ring-like support to create a gap from the vessel wall. Also, the membranes disclosed herein could be used with the various support embodiments disclosed. Those skilled in the art will envision many other possible variations that are within the scope and spirit of the disclosure as defined by the claims appended hereto.

What is claimed is:

1. An implantable device for regulating blood flow through a blood vessel, comprising:
   a) an elongated support dimensioned and configured to be implanted in a blood vessel, the support including axially spaced apart first and second support portions, and at least one linking member connecting the axially spaced apart portions to one another; and
   b) a valve membrane including a body portion and a neck portion extending therefrom, the body portion attached to one of the first and second support portions and the neck portion being attached to the other of the first and second support portions, the valve membrane adapted for movement between a first position wherein the body portion extends substantially across the elongated support with the neck portion in close proximity with a wall of the blood vessel inhibiting blood flow through the support, and a second position wherein the neck portion moves away from a wall of the blood vessel permitting blood flow through the support, in the first position the valve membrane having a convex outer surface and in the second position the valve membrane having a wavy shape.

2. An implantable device as recited in claim 1, wherein the first and second portions are substantially annular and have a wavy configuration.

3. An implantable device as recited in claim 1, wherein the support is formed at least in part from a shape memory alloy material.

4. An implantable device as recited in claim 1, wherein the valve membrane is formed at least in part from PTFE.

5. An implantable device as recited in claim 1, wherein the valve membrane is coated at least in part with an anti-clotting agent.

6. An implantable device as recited in claim 1, further comprising a suture extending between the first support portion and the valve membrane.

7. An implantable device as recited in claim 1, wherein the membrane includes first and second flaps formed by a folded edge for attachment to the support portions.

8. An implantable device as recited in claim 1, wherein the second portion includes an indent in the support to form a gap to enable backflow of blood when the membrane is in the second position.

9. An implantable device as recited in claim 1, wherein the support is formed from a laser cut tube.

10. An implantable device as recited in claim 1, wherein the support is formed from at least one wire.

11. An implantable device for regulating blood flow through a blood vessel, comprising:
    a) an elongated support dimensioned and configured to be implanted in a blood vessel, the support including first and second axially spaced apart portions and a curved linking member joining the first and second portions at about 90 degrees apart; and
    b) a valve membrane including a body portion and a neck portion extending therefrom, the body portion attached to one of the first and second support portions and the neck portion being attached to the other of the first and second support portions, the valve membrane adapted for movement between a first position wherein the body portion extends substantially across the elongated support with the neck portion in close proximity with a wall of the blood vessel inhibiting blood flow through the support, and a second position wherein the neck portion moves away from a wall of the blood vessel permitting blood flow through the support.

12. An implantable device as recited in claim 11, wherein the membrane includes a body portion and a narrower neck portion.

13. An implantable device as recited in claim 12, wherein the neck portion includes a first flap formed by a folded edge of the membrane and the body portion includes a second flap formed by a folded edge for attachment to the support.

14. The implantable device of claim 12, wherein the neck portion has a length at least equal to the radius of the first support portion.

15. The implantable device of claim 12, wherein the neck portion extends upwardly and outwardly in an arc extending away from the body portion.

16. The implantable device of claim 11, wherein the support is formed from a laser cut tube.

17. An implantable device as recited in claim 11, wherein the first and second portions of the support form substantially ring-like members, and the support is formed from two wires, the first wire forming part of the first substantially ring like member and one linking member and the second wire forming part of the second substantially ring-like member and another linking member.

18. The implantable device of claim 11, wherein each of the first and second axially spaced apart portions has a wavy configuration.

19. An implantable device for regulating flow within a body, comprising:
    a) an elongated support dimensioned and configured to be implanted in a tubular structure of the body, the support including axially spaced apart first and second support portions, and at least one linking member connecting the axially spaced apart portions to one another; and
    b) a valve membrane including a body portion and a neck portion extending therefrom, the body portion attached to one of the first and second support portions and the neck portion being attached to the other of the first and second support portions, the valve membrane adapted for movement between a first position wherein the body portion extends substantially across the elongated support with the neck portion in close proximity with a wall of the tubular structure inhibiting blood flow through the support, and a second position wherein the neck portion moves away from a wall of the tubular structure permitting blood flow through the support.

20. An implantable device as recited in claim 19, wherein the valve membrane is configured and adapted to move from the first position to the second position in a direction towards the wall of the tubular structure from a center of the tubular structure.

21. An implantable device as recited in claim 19, wherein the valve membrane is configured and adapted to move from the second position to the first position in a direction towards a center of the tubular structure from the wall of the tubular structure.

* * * * *